United States Patent [19]
Woods

[11] Patent Number: 4,790,847
[45] Date of Patent: Dec. 13, 1988

[54] INTRAOCULAR LENS IMPLANT HAVING EYE FOCUSING CAPABILITIES

[76] Inventor: Randall L. Woods, Rte. 4, Box 65, Clinton, Mo. 64735

[21] Appl. No.: 54,293

[22] Filed: May 26, 1987

[51] Int. Cl.⁴ .............................................. A61F 2/16
[52] U.S. Cl. ...................................................... 623/6
[58] Field of Search ........................................... 623/6

[56] References Cited

U.S. PATENT DOCUMENTS

| | | |
|---|---|---|
| 3,996,626 | 12/1976 | Richards et al. ............... 623/6 |
| 4,056,855 | 11/1977 | Kelman ........................ 623/6 |
| 4,074,368 | 2/1978 | Levy, Jr. et al. ............... 623/6 |
| 4,110,848 | 9/1978 | Jensen ......................... 623/6 |
| 4,253,199 | 3/1981 | Banko .......................... 623/6 |
| 4,254,509 | 3/1981 | Tennant ........................ 623/6 |
| 4,285,072 | 3/1981 | Morcher et al. ................. 623/6 |
| 4,370,760 | 2/1983 | Kelman ........................ 623/6 |
| 4,409,691 | 10/1983 | Levy ........................... 623/6 |
| 4,575,877 | 3/1986 | Herrick ........................ 623/6 |
| 4,615,701 | 10/1986 | Woods ......................... 623/6 |
| 4,662,882 | 5/1987 | Hoffer ......................... 623/6 |

OTHER PUBLICATIONS

"The Woods' Concept for Capsular Bag Placement", Copeland Intra Lenses, Inc., Randall Woods, D.O.

*Primary Examiner*—Ronald L. Frinks
*Attorney, Agent, or Firm*—Hovey, Williams, Timmons & Collins

[57] ABSTRACT

An intraocular lens is provided having focusing capabilities permitting shiftable focusing movement of the lens in response to normal ciliary muscle movement incident to changes in range between the eye and an object under observation. The lens is designed for surgical implantation within the capsule of an eye and includes an optic and rearwardly extending haptics oriented for central optic positioning and continuous anterior biasing of the optic against the anterior wall of the capsule. When distant objects are viewed and the ciliary muscle is retracted, the capsule is relatively discoid shaped thus moving the optic posteriorly and loading the haptics in compression. During near object viewing, when the ciliary muscle is contracted, the capsule assumes a relatively more spherical configuration and the loaded haptics urge the optic against the anterior capsule wall for proper focusing.

4 Claims, 2 Drawing Sheets

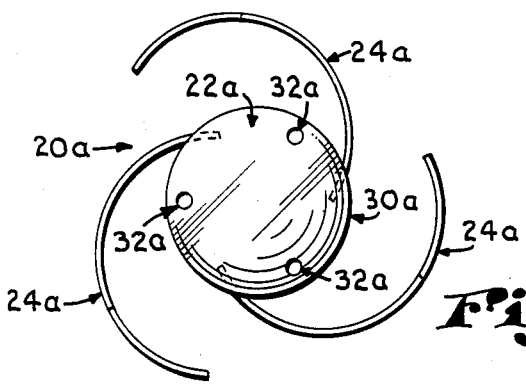
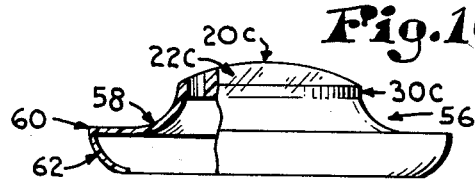
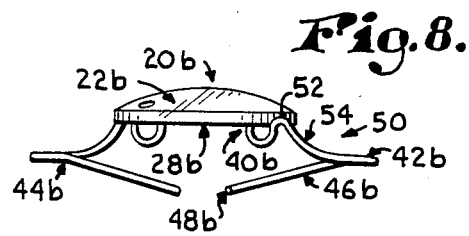
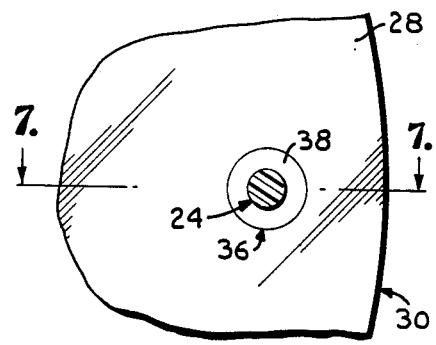
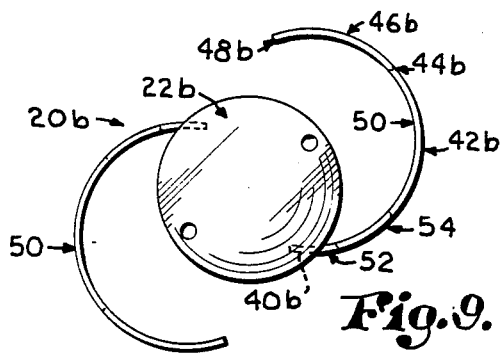
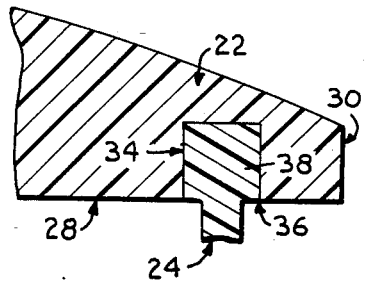
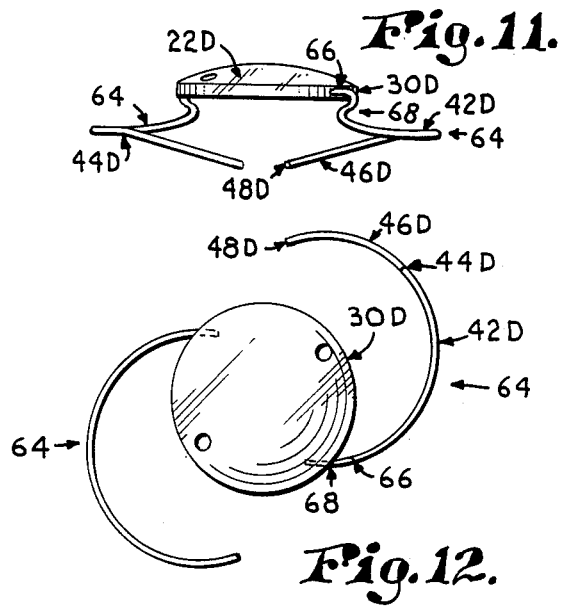

INTRAOCULAR LENS IMPLANT HAVING EYE FOCUSING CAPABILITIES

BACKGROUND OF THE INVENTION

1. Field of the Invention

This invention relates to an improved focusing intraocular lens which can be surgically implanted as a replacement for the natural crystalline lens in the eyes of cataract patients. More particularly, it is concerned with a strategically configured lens including an optic and one or more haptics constructed to position the lens within the capsule of the eye, the haptics continuously urging the optic against the anterior face of the capsule and thereby moving the lens during normal ciliary muscle movement incident to focusing.

2. Description of the Prior Art

Cataracts occur when the crystalline lens of the eye becomes opaque. The cataracts may be in both eyes and, being a progressive condition, may cause fading vision and eventual blindness. Cataracts were once surgically removed along with the anterior wall of the capsule of the eye. The patient then wore eyeglasses or contact lenses which restored vision but did not permit focusing and gave only limited depth perception.

The first implant of a replacement lens within the eye occurred in 1949 and attempted to locate the replacement lens in the posterior chamber of the eye behind the iris. Problems such as dislocation after implantation forced abandonment of this approach, and for some period thereafter intraocular lenses were implanted in the anterior chamber of the eye. Lenses implanted in the anterior chamber include those shown in U.S. Pat. Nos. 3,673,616, 3,906,551, 3,922,728, 3,925,825, 3,971,073, 3,975,779, 3,979,780, 3,986,214, 3,996,627, 4,010,496, 4,056,555, 4,073,015, 4,077,071, 4,079,470, 4,087,866, 4,254,509, and 4,370,760.

Others returned to the practice of inserting the lens in the area of the eye posterior of the iris, known as the posterior chamber. This is the area where the patient's natural crystalline lens is located. When the intraocular lens is located in this natural location, substantially normal vision may be restored to the patient and the problems of forward displacement of vitreous humor and retina detachment encountered in anterior chamber intraocular lenses are less likely to occur. Lenses implanted in the posterior chamber include those shown in U.S. Pat. Nos. 3,718,870, 3,866,249, 3,913,148, 3,925,825, 4,014,049, 4,041,552, 4,053,953, and 4,285,072. None of these lenses had focusing capability.

Lenses capable of focusing offer the wearer the closest possible substitute to the crystalline lens. U.S. Pat. No. 4,254,509 to Tennant discloses a lens which moves in an anterior direction upon contraction of the ciliary body and which is located anterior to the iris. Though providing focusing capabilities, it presents the same disadvantages as other anterior chamber lenses. U.S. Pat. No. 4,253,199 to Banko approaches the problem of providing a focusable lens differently, by providing a replacement lens of deformable material sutured to the ciliary body. This lens functions much as the original crystalline lens but risks bleeding from the sutures and requires, as do the prior references, removal of the anterior wall of the capsule.

U.S. Pat. No. 4,409,691 to Levy is asserted to provide a focusable intraocular lens positioned within the capsule. This lens is located in the posterior area of the capsule and is biased toward the fovea or rear of the eye.

It is believed the Levy lens is deficient because it requires the ciliary muscle to exert force through the zonules on the capsule to compress the haptics inward driving the optic forward for near vision. However, the ciliary muscles do not exert any force during contraction because the zonules, being flexible filaments, exert only tension, not compression on the capsule. The natural elasticity of the lens causes the capsule to become more spherical upon contraction of the ciliary muscle. Thus there is no inward force exerted on the capsule to compress the haptics of the Levy lens, and therefore accommodate for near vision. Even if such force were somehow available, the Levy lens' haptics are loaded inward when accommodating for near vision. Since accomodation for near vision is the normal status of the capsule, the Levy lens' haptics are normally loaded, reducing the fatigue life of the springlike haptics.

SUMMARY OF THE INVENTION

The present invention provides a superior focusable intraocular lens which is designed for positioning within the capsule and includes specialized structure for biasing of the optic portion of the intraocular lens against the anterior wall of the capsule. Such continuous contact against the anterior wall of capsule not only provides additional support for the lens but serves, in co-operation with the natural movement of the anterior capsule wall incident to ciliary muscle movement, for focusing the lens.

In preferred forms, the intraocular lens in accordance with the present invention includes an optic presenting a convex anterior face and a posterior face with a haptic or series of haptics extending from posterior surface or side marginal edge of the optic. The optic and each haptic is constructed of biologically inert material to prevent absorption by the body of the patient. The haptics are advantageously of thin, flexible, arcuate configuration and are connected to the posterior surface or side marginal edge of the optic and extend therefrom both radially and rearwardly to contact the portion of the capsule adjacent the zonular fibers. The haptic or haptics thus center the optic in the eye behind the pupil and hold the optic against tha anterior wall of the capsule. This haptic structure enables the optic to move forward as the ciliary muscles contract to focus on objects which are relatively near the eye, and, conversely, to move rearwardly as the ciliary muscles retract to focus on objects at a greater distance.

Alternate embodiments of the lens provide different configurations and placement of the haptics. The number of haptics may increase to two or three to provide additional support within the capsule. A U- or S-shaped bend may be formed in the haptics to enhance their biasing capability. Finally, the haptics may extend from the side of the optic rather than depend from the posterior face.

Alternatively, a continuous skirt may replace the haptics as a positioning and biasing means. The skirt may surround the lens and extend to a capsule-engaging biasing flange to contact the capsule opposite the zonular fibers. The skirt margin engages the capsule wall adjacent the zonular fibers. The flange extends posteriorly from the skirt margin and engages the posterior capsule wall adjacent the zonular region.

BRIEF DESCRIPTION OF THE DRAWINGS

FIG. 5 is a front view of an alternate embodiment of the lens having three haptics.

FIG. 6 is an enlarged fragmentary view showing the location of a haptic on the optic;

FIG. 7 is a sectional view of the haptic taken along line 7—7 of FIG. 6 which illustrates the mounting of the haptic on the optic;

FIG. 8 is a side view of a lens having a pair of U-shaped haptics;

FIG. 9 is a front view of a lens having a pair of U-shaped haptics;

FIG. 10 is a side view in partial vertical section and with parts broken away showing a lens with a haptic in the form of a continuous skirt surrounding the optic;

FIG. 11 is a side view of a lens with a pair of S-shaped side mounted haptics; and FIG. 12 is a front view of an optic with a pair of S-shaped side mounted haptics.

DESCRIPTION OF THE PREFERRED EMBODIMENTS

Figure 1:
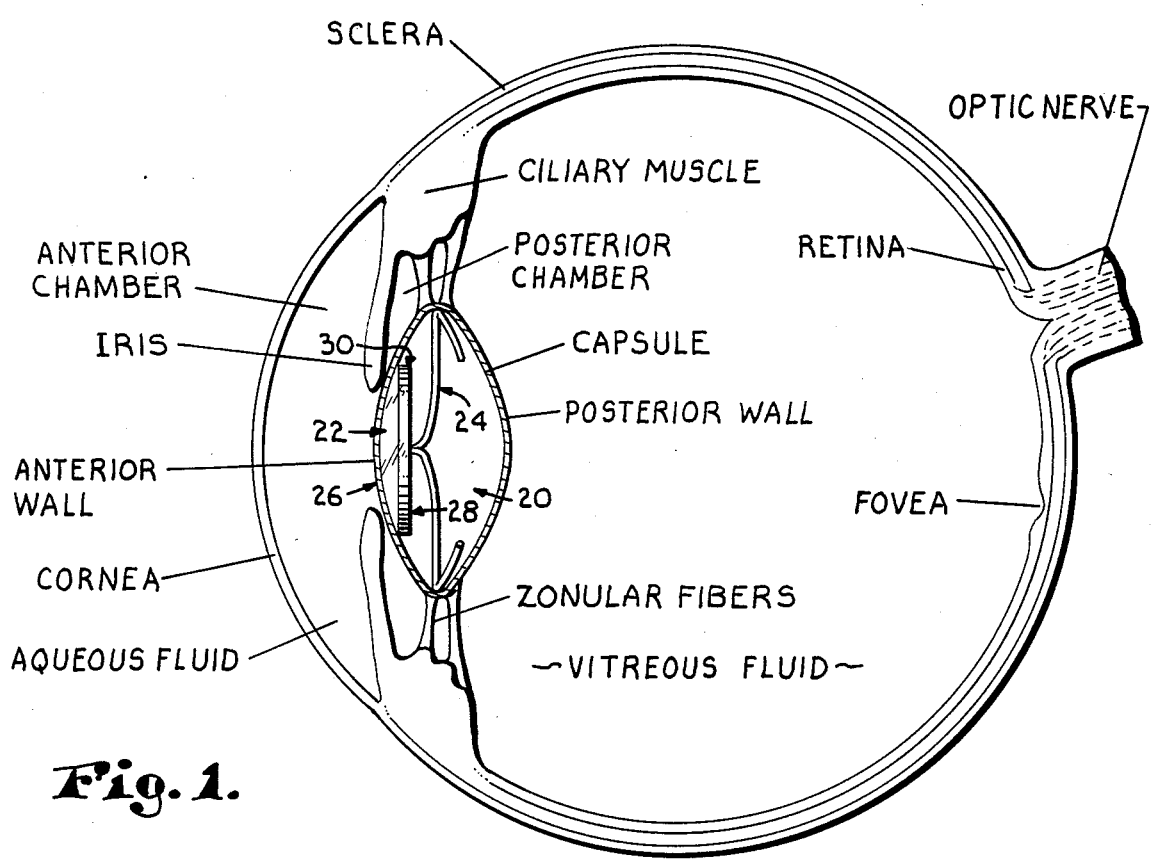
FIG. 1 is a vertical sectional view showing placement of the lens of the invention within the capsule of an eye, with the eye focused on an object near the viewer.
Figure 2:
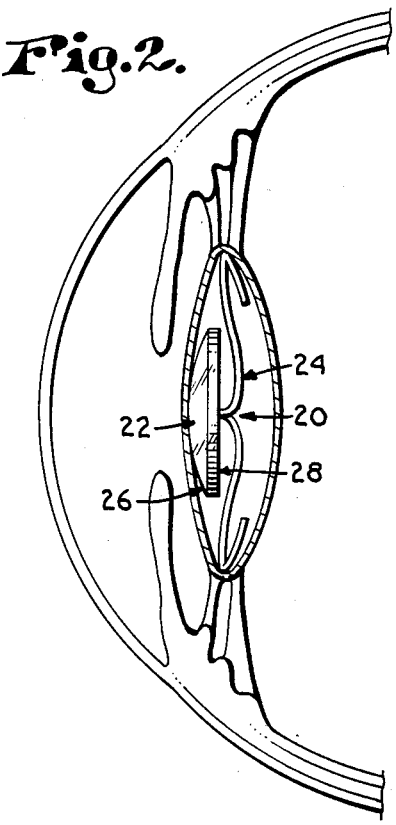
FIG. 2 is a partial vertical sectional view showing the location of the lens of FIG. 1 within the capsule of the eye, focused on an object distant from the viewer.

Referring now to the drawings, the present invention is in the form of an intraocular lens for surgical replacement of the human lens in the treatment of cataracts in the human eye. FIG. 1 shows the various components of the human eye pertinent to this invention. The frontal portion of the human eye is covered by the coronea which encloses the anterior chamber. The anterior chamber contains aqueous fluid and is bounded at the rear by the iris. The iris opens and closes to admit appropriate quantities of light into the inner portions of the eye. The portion of the eye which ordinarily contains the crystalline lens is called the capsule. When the eye focuses, the capsule changes shape to appropriately distribute the light admitted through the cornea and iris to the retina at the posterior portion of the eye. The retina at the rear of the eye is composed of rods and cones which act as light receptors. The rodless portion of the retina which provides for acute vision is called the fovea. The outside of the posterior portion of the dye is known as the sclera which joins into and forms a portion of the covering for the optic nerve. Images received by the retina are transmitted through the optic nerve to the brain. The area between the retina and the capsule is occupied by vitreous fluid.

Occular adjustments for sharp focusing of objects viewed at different distances is accomplished by the action of the ciliary muscle on the capsule and crystalline lens through the zonular fibers. The ciliary muscle contracts, thereby making the capsule and lens more spherical, to view objects that are nearer the viewer. When the ciliary muscle retracts and pulls on the zonular fibers to make the capsule and lens more discoid, objects at a distance can be viewed in proper focus.

Turning now to FIGS. 1–4, a lens 20 includes a central optic 22 and at least one haptic 24. The optic 22 includes an anterior surface 26, a posterior surface 28, and a side marginal edge 30. Anterior surface 26 is usually convex and posterior surface 28 normally planar, though the shape of these surfaces can be varied for different applications. Optic 22 is also provided with a pair of mounting receptacles 32 adapated to receive the special tools necessary for placement of the lens 20. Mounting receptacles 32 are typically located adjacent side marginal edge 30 on opposite sides of anterior surface 26.

FIGS. 6 and 7 show haptics 24 mounted on the posterior surface 28 of the lens. A mounting aperture 34 in the posterior surface 28 is located adjacent side marginal edge 30. An edge 36 is created at the juncture of the mounting aperture 34 and the posterior surface 28. Mounting aperture 34 will normally be cylindrical and of a greater diameter than the diameter of haptic 24. Haptic 24 is provided with a head 38 adapted to be securely received by mounting aperture 34 and haptic 24 is normally constructed of a softer material than optic 22. Head 38 thus prevents edge 36 from cutting haptic 24.

Figure 3:
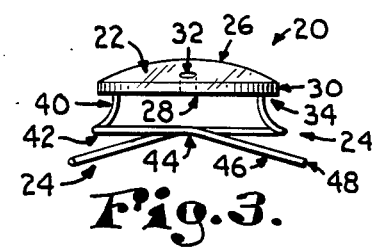
FIG. 3 is a side elevational view of one embodiment of the lens having two haptics.
Figure 4:
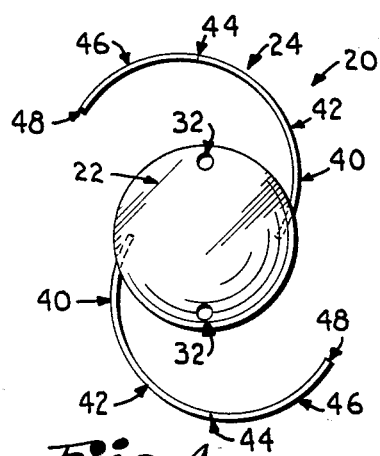
FIG. 4 is a front view of the lens of FIG. 3.

Returning to FIGS. 3 and 4, haptics 24 are mounted 180 degrees apart and 90 degrees from receptacles 32. The haptics 24 are shown in FIGS. 3 and 4 as continuously arcuate filaments which extend posteriorly and radially outwardly from the posterior surface 28 of the optic 22 to engage the capsule wall posterior to the anterior surface 26 of optic 22. Haptics 24 are integrally constructed of flexible, resilient, biologically inert synthetic resin material. Three sections make up the haptics 24 posterior of mounting head 38 as shown in FIGS. 3 and 4. A depending length 40 is arcuate both in posterior and radical directions. Continuing radially outward, haptic 24 transitions from depending length 34 to radial stretch 42 when the tangent of depending length 40 becomes parallel to the posterior surface 28 of the optic 22. At bend 44, the haptic 24 resumes a posterior bias. That section of haptic 24 posterior and radially outward of bend 44 is referred to herein as a biasing reach 46 which ends at terminus 48.

FIG. 5 shows lens 20a similar in all respects to the lens previously shown in FIGS. 1 through 4 with the exception that it mounts three haptics 24a. The haptics 24a are spaced equidistantly around the optic 22a in mounted intermediate receptacles 32a and adjacent the side marginal edge 30a. It is thus readily apparent that any number of haptics 24a may be mounted on 22a.

FIGS. 8 and 9 reflect an alternate embodiment shown as lens 20b. Haptic 50 is mounted on optic 22b which is similar in configuration to the lenses shown in FIGS. 1 through 4. Depending length 40b is interrupted in its posterior path by bight 52 of U-shaped segment 54. The bight 52 returns the path of haptic 50 anterior to the posterior surface 28b of optic 22b before the haptic 50 returns in a posterior path. The U-shaped segment 54 provides haptic 50 with an improved biasing capability. Following the U-shaped section 54, haptic 50 continues into its radial stretch 42b, bend 44b and biasing reach 46b before ending at terminus 48b.

Lens 20c is shown in FIG. 10 with an alternate positioning means. A parabolic skirt 56 is connected to optic 22c and extends radially and posteriorly from the side marginal edge 30c of the optic 22c. Optic 22c is similar to optics 22, 22a and 22b except skirt 56 is mounted to side marginal edge 30c eliminating the need for a mounting aperture. The skirt 56 is arcuate in cross section and comprises a ring 58 and an edge 60. Depending posteriorly and radially inward from the edge 60 is flange 62 for engaging the capsular wall posterior to the zonular fibers. Flange 62 continuously surrounds edge 60 of the skirt 56 and thus uniformly contacts the posterior capsule wall.

FIGS. 11 and 12 illustrate a further modification of the lens design. Haptic 64 is mounted on optic 22d at the side marginal edge 30d into mounting aperture 66. Optic 22d is similar in construction to optics 20-20c except that mounting aperture 34d is located on the side marginal edge 30d of optic 22d. Haptic 64 presents an S-shaped segment 68 which depends posteriorly from the side marginal edge 30d of optic 22d. The S-shaped segment 68 provides additional biasing capability. As shown in FIGS. 11 and 12, haptic 64 continues from S-shaped segment 68 into radial stretch 42d, bend 44d and biasing reach 46d to terminus 48d, as in the haptics shown in FIGS. 1-5, 8 and 9.

Returning to FIGS. 1 through 4, intraocular lens 20 substitutes both locationally and functionally for the original, natural, crystalline lens. An ophthalmic surgeion makes incisions both in the cornea and the anterior wall of the capsule to implant the lens in the eye. Haptics 24 are compressed against optic 22 to permit entry through the smallest possible incision in the cornea and capsule. During this procedure, a surgical instrument grasps the lens 20 by receptacles 32 for placement and positioning within the capsule. The surgeon then closes the entrance incision and correctly positions the haptics 24, engaging the biasing reaches 46 against the posterior wall of the capsule and posterior to the anterior surface 26 of optic 22. Haptics 24 therefore bias the optic 22 against the anterior wall of the capsule. Biasing reach 46 of haptic 24 shown in FIGS. 1 through 5, 8, 9, 11 and 12 extends from radial stretch 42 and engage the posterior capsule wall opposite the zonular fibers. Thus haptics 24 accomplish both a centering and biasing function. In the alternate embodiment shown in FIG. 10, skirt 56 extends radially and posteriorly from optic 22c until skirt margin 60 contacts the capsule wall opposite the zonular fibers. Flange 62 thus engages the posterior wall of the capsule adjacent the zonular fibers and maintain optic 22c in its proper location, biasing it against the anterior wall of the capsule. Both biasing reach 46 and edge 60 engage the capsule posterior to the anterior surface 26 and in the preferred embodiment remain posterior to the posterior surface 28 of optic 22.

Implantation of the present lens 20 restores normal vision because not only does the lens 20 replace the patient's occluded natural lens, but the normaly ciliary muscle responses cooperate with the lens 20 during focusing. In FIG. 1, the focal length between the posterior surface 28 of the optic 22 and the fovea is greater t permit viewing of nearby objects. The focal length is greater because the ciliary muscle has contracted, making the capsule more spheroid and permitting the optic 22 to move anteriorly. The lens of the present construction thus follows the eye's natural physiology for focusing to provide a substitute means of optical accommodation. When the object under observation becomes more distant, the sensory cells within the retina signal the ciliary muscle to relax, thus pulling on the zonular fibers to make the capsule more discoid. In so doing, the horizontal depth of the capsule is narrowed and skirt 56 or the haptics 24 are loaded. Because the haptics 24 bias the optic 22 in an anterior direction, the haptics 24 or skirt 56 load as they yield to permit the optic 22 to move posteriorly as the capsule becomes more discoid. The focal length between the posterior surface 28 of the optic 22 and the fovea is thus shortened, and the object remains in focus. If the object under observation reapproaches the eye, the ciliary muscles contract, lessening, tension on the zonular fibers. Haptics 24 or skirt 56 then unload and urge optic 22 forward against the anterior face of the capsule wall. The focal length between the posterior surface 28 of the optic 22 and the fovea is thus increased, and the object remains in focus.

I claim:

1. An intraocular lens having focusing capabilities for implantation entirely within the confines of the capsule of a human eye between the anterior and posterior capsule walls, the eye also having a fovea behind said capsule, a ciliary muscle disposed about the capsule, and zonular fibers interposed between the ciliary muscle and capsule, said lens comprising:

an optic presenting an anterior surface, a posterior surface, and a side marginal edge; and positioning means operably coupled with said optic, extending posteriorly of said posterior surface of the optic and outwardly of said marginal edge thereof, and presenting an outboard capsule-engaging portion spaced posteriorly of said optic anterior surface, said capsule-engaging portion including a structure for continuous anterior biasing of said optic such that the optic anterior surface is in constant, biased engagement with said anterior capsule wall at all times during operation of the lens, said positioning means comprising an arcuate in cross section skirt extending posteriorly and radially outwardly from said optic, the outer margin of said skirt lying in one plane, there being a flange extending posteriorly from the edge of said skirt's margin.

2. The lens of claim 1, said optic presenting a convex anterior surface.

3. The lens of claim 1, said skirt being formed of yieldable synthetic resin material.

4. The lens of claim 1, said skirt being a continuous circumscribing member surrounding said optic.

* * * * *